(12) United States Patent
Abrams et al.

(10) Patent No.: US 10,695,333 B2
(45) Date of Patent: Jun. 30, 2020

(54) PHARMACEUTICAL COMBINATION COMPRISING LSZ102 AND ALPELISIB

(71) Applicant: NOVARTIS AG, Basel (CH)

(72) Inventors: Tinya Abrams, Acton, MA (US); Larry Alexander Gaither, Bradford, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/204,471

(22) Filed: Nov. 29, 2018

(65) Prior Publication Data

US 2019/0167652 A1 Jun. 6, 2019

Related U.S. Application Data

(60) Provisional application No. 62/771,757, filed on Nov. 27, 2018, provisional application No. 62/593,760, filed on Dec. 1, 2017.

(51) Int. Cl.
| | |
|---|---|
| *A61K 31/4439* | (2006.01) |
| *A61P 35/00* | (2006.01) |
| *A61K 31/381* | (2006.01) |
| *C07D 409/06* | (2006.01) |

(52) U.S. Cl.
CPC ........ *A61K 31/4439* (2013.01); *A61K 31/381* (2013.01); *A61P 35/00* (2018.01); *C07D 409/06* (2013.01)

(58) Field of Classification Search
None
See application file for complete search history.

(56) References Cited

U.S. PATENT DOCUMENTS

| | | | |
|---|---|---|---|
| 2015/0080483 A1 | 3/2015 | Hanebuth et al. | |
| 2016/0375033 A1* | 12/2016 | Edgar | A61K 31/553 424/133.1 |
| 2019/0142796 A1* | 5/2019 | Abrams | A61K 31/519 |

FOREIGN PATENT DOCUMENTS

| | | |
|---|---|---|
| JP | 2016523253 | 8/2016 |
| WO | WO 2007030360 | 3/2007 |
| WO | WO 2015022609 | 2/2015 |
| WO | WO 2015028409 | 3/2015 |
| WO | WO 2015080438 | 4/2015 |
| WO | WO 2015136016 | 9/2015 |
| WO | WO 2016176666 | 11/2016 |
| WO | WO-2017168303 A1 * | 10/2017 ........... C07C 269/06 |
| WO | WO 2018129387 | 7/2018 |

OTHER PUBLICATIONS

Tria, George S. et al., Discovery of LSZ102, a Potent, Orally Bioavailable Selective Estrogen Receptor Degrader (SERD) for the Treatment of Estrogen Receptor Positive Breast Cancer, Journal of Medicinal Chemistry, vol. 61, No. 7, Mar. 22, 2018. pp. 2837-2864, XP055564421, US ISSN 0022-2623, DOI: 10.1021/acsjmedchem. 7b01682 abstract.

Juric, D. et al, Phase I/Ib study of the SERD LSZ102 alone or in combination with ribociclib in ER+ breast cancer, Cancer Research, American Association for Cancer Research, US vol. 78, No. 4, Suppl. 1, Feb. 1, 2018, pp. 3, XP009511171, ISSN 1538-744 SABCS17-P5-21-04.

Blackburn, Sophie A. et al., Fulvestrant for the treatment of advanced breast cancer, School of Medicine, University of Nottingham, Nottingham, UK, Expert Review of Anticancer Therapy (2018), 18(7), pp. 619-628.

Wardell, Suzanne E. et al., Efficacy of SERD/SERM Hybrid-CDK4/6 inhibitor Combinations in Models of Endocrine Therapy-Resistant Breast Cancer, Department of Pharmacology & Cancer Biology, Duke University School of Medicine, Durham, NC, Clinical Cancer Research (2015), 21(22), pp. 5121-5130.

Nichols, Mark, New directions for drug-resistant breast cancer: the CDK/6 inhibitors; Department of Pharmacology & Chemical Biology, School of Medicine, University of Pittsburgh, Pittsburgh, PA, Future Medicinal Chemistry, (2015), 7 (12), pp. 1473-1481.

Weir, Hazel M. et al., AZD9496, An Oral Estrogen Receptor inhibitor That Blocks the Growth of ER-Positive and ESR1-Mutant Breast Tumors in Preclinical Models, AstraZeneca, Oncology iMed, Macclesfield; UK, Cancer Research, (2016), 76(11), pp. 3307-3318.

\* cited by examiner

*Primary Examiner* — James D. Anderson
*Assistant Examiner* — Stephanie K Springer
(74) *Attorney, Agent, or Firm* — David K. Cheung

(57) ABSTRACT

The present invention relates to a pharmaceutical combination comprising LSZ102 and alpelisib; pharmaceutical compositions comprising the same; and methods of using such combinations and compositions in the treatment or prevention of conditions in which degradation of estrogen receptors combined with PI3K inhibition is beneficial in, for example, the treatment of cancers.

4 Claims, 14 Drawing Sheets

Fulves (Fulvestrant), Tam (Tamoxifen)

Synergy score = 6.1

PHARMACEUTICAL COMBINATION COMPRISING LSZ102 AND ALPELISIB

FIELD OF THE INVENTION

The present invention relates to a pharmaceutical combination comprising LSZ102 and alpelisib; pharmaceutical compositions comprising the same; and methods of using such combinations and compositions in the treatment or prevention of conditions in which degradation of estrogen receptors combined with PI3K inhibition is beneficial, for example, in the treatment of cancers.

BACKGROUND OF THE INVENTION

Estrogens play a critical role in the development of female and male reproductive tissues and contributes to the development and progression of estrogen receptor diseases or disorders such as breast, ovarian, colon, prostate, endometrial and uterine cancers.

Estrogen receptor (ERα)-positive diseases such as breast cancer are usually treated with a selective estrogen receptor modulator (SERM) or an aromatase inhibitor (AI). While these therapies have proven effective at reducing the incidence of progression of breast cancer, some patients exhibit treatment resistance and progress to advanced metastatic breast cancer.

Treatment resistance results, in part, from the evolution of tumors to a state of hypersensitivity to low estrogen levels (AI treatment) or development of dependence upon the antiestrogen for activation of transcription (SERM treatment). SERDs degrade the receptor, effectively eliminating ERα expression and in so doing circumvent the underlying mechanisms of resistance that develop to antiendocrine monotherapy. Further, clinical and preclinical data show that a significant number of the resistance pathways can be circumvented by the use of an antiestrogen that exhibits SERD activity.

The PI3K proteins comprise a family of lipid kinases that regulate nutrient uptake, metabolism, cellular proliferation and survival. The best studied class of PI3Ks in cancer biology is the Class IA PI3Ks which include p110α, p110β, and p110δ. Mutations in the PIK3CA gene are present in 28-47% of HR+ breast cancer. The PI3K isoform, p110α, is constitutively activated in human cancers and particularly critical in breast cancer. Oncogenic growth signals are also relayed through p110β and p110δ, though their contribution to breast cancer specifically is less well defined. Critically, ER signaling and PI3K activity coregulate one another. Inhibition of either results in upregulation of the other thus simultaneous inhibition of both to achieve maximal antitumor activity is a rational approach.

The combination of the present invention, LSZ102 and alpelisib, can be used as therapies for the treatment of estrogen receptor diseases or disorders, for example, ovulatory dysfunction, uterine cancer, endometrium cancer, ovarian cancer, endometriosis, osteoporosis, prostate cancer, benign prostatic hypertrophy, estrogen receptor alpha (ERα)-positive breast cancer, in particular ERα-positive breast cancer exhibiting de novo resistance to existing anti-estrogens and aromatase inhibitors.

SUMMARY OF THE INVENTION

The present invention provides for a pharmaceutical combination comprising:

(a) (E)-3-(4-((2-(2-(1,1-difluoroethyl)-4-fluorophenyl)-6-hydroxybenzo[b]thiophen-3-yl)oxy)phenyl)acrylic acid (LSZ102), or a pharmaceutically acceptable salt thereof, having the structure:

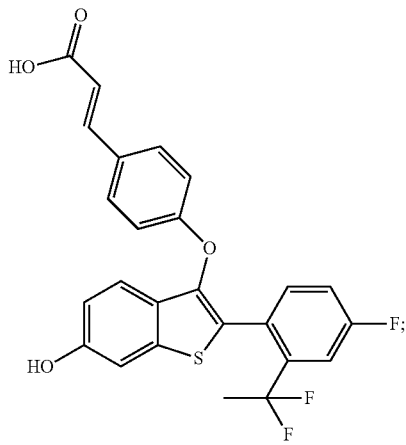 [SMILES: CC(F)(F)c1cc(F)ccc1-c1sc2cc(O)ccc2c1Oc1ccc(/C=C/C(=O)O)cc1]

and (b) (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide (alpelisib or BYL719), or a pharmaceutically acceptable salt thereof, having the structure:

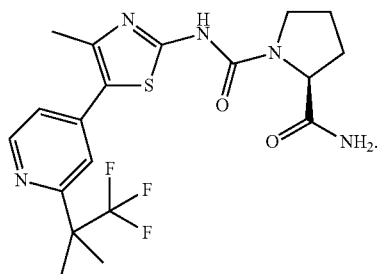 [SMILES: Cc1nc(NC(=O)N2CCC[C@H]2C(N)=O)sc1-c1ccnc(C(C)(C)C(F)(F)F)c1]

Combinations of LSZ102, or a pharmaceutically acceptable salt thereof, and alpelisib, or a pharmaceutically acceptable salt thereof, will also be referred to herein as a "combination of the invention".

In another embodiment of the combination of the invention, LSZ102 or a pharmaceutically acceptable salt thereof and alpelisib, or a pharmaceutically acceptable salt thereof, are in the same formulation.

In another embodiment of the combination of the invention, LSZ102 or a pharmaceutically acceptable salt thereof and alpelisib or a pharmaceutically acceptable salt thereof are in separate formulations.

In another embodiment, the combination of the invention is for simultaneous or sequential (in any order) administration. The combination can be administered in a single dosage form or in separate dosage form.

In another embodiment is a method for treating cancer in a subject in need thereof comprising administering to the subject a therapeutically effective amount of the combination of the invention.

In a further embodiment of the method, the cancer is estrogen receptor alpha (ERα) positive breast cancer.

In a further embodiment of the method, the cancer is selected from ovarian, endometrial, prostate, uterine, cervical and lung cancers.

In a further embodiment, the combination of the invention provides for a use in the manufacture of a medicament for treating estrogen receptor alpha (ERα) positive breast cancer.

In a further embodiment, the combination of the invention provides for a use in the manufacture of a medicament for treating a cancer selected from ovarian, endometrial, prostate, uterine, cervical and lung cancers.

In another embodiment is a pharmaceutical composition comprising the combination of the invention.

In a further embodiment, the pharmaceutical composition further comprises one or more pharmaceutically acceptable excipients.

DEFINITIONS

Figure 1:
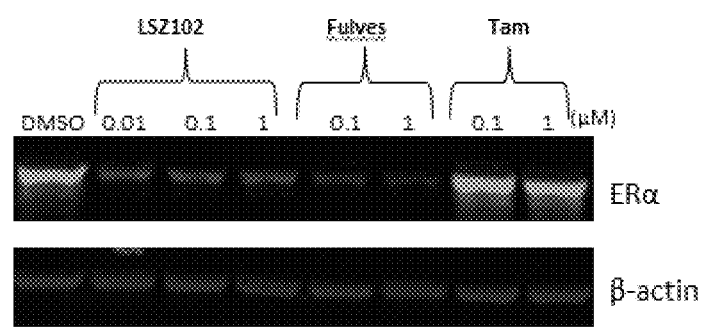
FIG. 1: Comparison of LSZ102, fulvestrant and tamoxifen on the promotion of ER degradation in MCF-7 cells.

The general terms used hereinbefore and hereinafter preferably have within the context of this disclosure the following meanings, unless otherwise indicated, where more general terms whereever used may, independently of each other, be replaced by more specific definitions or remain, thus defining more detailed embodiments of the invention:

"ESR1 mutations" are estrogen receptor gene (ESR1) mutations. Mutations result in ligand independent ER activity. Several mutations have been identified that modify the ligand binding domain of the ER. These mutations include, but are not limited to, D538G, E380Q and Y537S/N/C, representing more than 80% of the ESR1 mutations. These mutations are an acquired molecular event since they are almost absent in primary BC tumor (<2%). ESR1 mutations are common in patients who have received aromatase inhibitors in a metastatic setting. Mutations occur in 9% of early metastatic ER+ disease (Y537N/S and D538G) and 20% in late metastatic ER+ breast cancer (Y537C/N/S and D538G). Compared to wild-type, tumor growth is higher with D538G and Y537S mutations.

The term "subject" or "patient" as used herein is intended to include animals, which are capable of suffering from or afflicted with a cancer or any disorder involving, directly or indirectly, a cancer. Examples of subjects include mammals, e.g., humans, apes, monkeys, dogs, cows, horses, pigs, sheep, goats, cats, mice, rabbits, rats, and transgenic non-human animals. In an embodiment, the subject is a human, e.g., a human suffering from, at risk of suffering from, or potentially capable of suffering from cancers.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present disclosure, the term "treat" also denotes to arrest, delay the onset (i.e., the period prior to clinical manifestation of a disease) and/or reduce the risk of developing or worsening a disease.

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The combination of the invention, LSZ102 or alpelisib, is also intended to represent unlabeled forms as well as isotopically labeled forms of the compounds. Isotopically labeled compounds have one or more atoms replaced by an atom having a selected atomic mass or mass number. Examples of isotopes that can be incorporated into LSZ102 and alpelisib include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{123}I$, $^{124}I$, $^{125}I$ respectively. The invention includes isotopically labeled LSZ102 and alpelisib, for example into which radioactive isotopes, such as $^3H$, and $^{14}C$, or non-radioactive isotopes, such as $^2H$ and $^{13}C$, are present. Isotopically labelled LSZ102 and alpelisib are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, LSZ102 labeled with $^{18}F$ may be particularly desirable for PET or SPECT studies. Isotopically-labeled compounds of the invention can generally be prepared by conventional techniques known to those skilled in the art or by processes analogous to those described in the accompanying Examples using appropriate isotopically-labeled reagents.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of either LSZ102 or alpelisib. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in LSZ102 or alpelisib is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

DESCRIPTION OF PREFERRED EMBODIMENTS

LSZ102 is an investigational agent that is an orally bioavailable small molecule that has mixed SERD and SERM activity, with both anti-estrogenic and pro-estrogenic effects in animals. In breast cancer cell lines in vitro, LSZ102 has shown potent ER antagonism and degradation activity.

The PI3K inhibitor (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (also referred to herein as "alpelisib" or "BYL719") is a specific 2-carboxamide cycloamino urea derivative compound that potently and selectively targets the alpha (α)-isoform of class IA PI3K and has the following chemical structure:

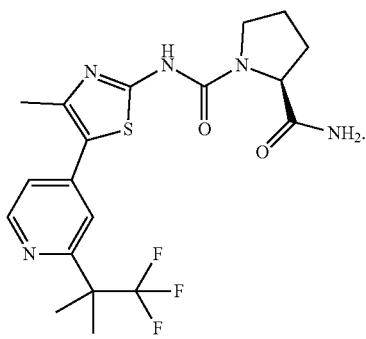 [SMILES: Cc1nc(NC(=O)N2CCC[C@H]2C(N)=O)sc1-c1ccnc(C(C)(C)C(F)(F)F)c1]

(S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) and its pharmaceutically acceptable salts are described in PCT Application No. WO2010/029082, which is hereby incorporated by reference in its entirety, and methods of its preparation have been described, for example, in Example 15 therein. Preferably, Compound (I) is in the free base form.

In one embodiment, with respect to the pharmaceutical combination of the invention, is a pharmaceutical combination comprising (E)-3-(4-((2-(1,1-difluoroethyl)-4-fluorophenyl)-6-hydroxybenzo[b]thiophen-3-yl)oxy)phenyl)acrylic acid, or pharmaceutically acceptable salt thereof, and (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide, or a pharmaceutically acceptable salt thereof.

In a further embodiment, (E)-3-(4-((2-(2-(1,1-difluoroethyl)-4-fluorophenyl)-6-hydroxybenzo[b]thiophen-3-yl)oxy)phenyl)acrylic acid, or a pharmaceutically acceptable salt thereof, and (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide, or a pharmaceutically acceptable salt thereof, are administered separately, simultaneously or sequentially, in any order.

In a further embodiment, the pharmaceutical combination is for oral administration.

In a further embodiment, (E)-3-(4-((2-(2-(1,1-difluoroethyl)-4-fluorophenyl)-6-hydroxybenzo[b]thiophen-3-yl)oxy)phenyl)acrylic acid is in an oral dose form.

In a further embodiment, (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide is in an oral dose form.

In another embodiment, is a pharmaceutical composition comprising a pharmaceutical combination of (E)-3-(4-((2-(2-(1,1-difluoroethyl)-4-fluorophenyl)-6-hydroxybenzo[b]thiophen-3-yl)oxy)phenyl)acrylic acid, or pharmaceutically acceptable salt thereof, and (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide, or a pharmaceutically acceptable salt thereof and at least one pharmaceutically acceptable carrier.

In a further embodiment, is a pharmaceutical combination of (E)-3-(4-((2-(2-(1,1-difluoroethyl)-4-fluorophenyl)-6-hydroxybenzo[b]thiophen-3-yl)oxy)phenyl)acrylic acid, or pharmaceutically acceptable salt thereof, and (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide, or a pharmaceutically acceptable salt thereof, for use in the treatment of a cancer, preferably breast cancer.

In a further embodiment, is a pharmaceutical combination of (E)-3-(4-((2-(2-(1,1-difluoroethyl)-4-fluorophenyl)-6-hydroxybenzo[b]thiophen-3-yl)oxy)phenyl)acrylic acid, or pharmaceutically acceptable salt thereof, and (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide, or a pharmaceutically acceptable salt thereof, for use in the treatment of wild-type ER+ breast cancer.

In another embodiment, is a pharmaceutical combination of (E)-3-(4-((2-(2-(1,1-difluoroethyl)-4-fluorophenyl)-6-hydroxybenzo[b]thiophen-3-yl)oxy)phenyl)acrylic acid, or pharmaceutically acceptable salt thereof, and (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide, or a pharmaceutically acceptable salt thereof, for use in the treatment of ESR1 mutant ER+ breast cancer.

In a further embodiment, the ESR1 mutation is an MCR7 expressing ESR1 mutation.

In a further embodiment, the ESR1 mutations are selected from the group consisting of D538G, E380Q, Y537S, Y537N and Y537C.

In a further embodiment, the ESR1 mutations are selected from the group consisting of D538G and Y537S.

In another embodiment, is a use of the pharmaceutical combination of (E)-3-(4-((2-(2-(1,1-difluoroethyl)-4-fluorophenyl)-6-hydroxybenzo[b]thiophen-3-yl)oxy)phenyl)acrylic acid, or pharmaceutically acceptable salt thereof, and (S)-Pyrrolidine-1,2-dicarboxylic acid 2-amide 1-({4-methyl-5-[2-(2,2,2-trifluoro-1,1-dimethyl-ethyl)-pyridin-4- yl]-thiazol-2-yl}-amide, or a pharmaceutically acceptable salt thereof, for the manufacture of a medicament for the treatment of a cancer, preferably breast cancer.

In another embodiment, is a use of the pharmaceutical combination of (E)-3-(4-((2-(2-(1,1-difluoroethyl)-4-fluorophenyl)-6-hydroxybenzo[b]thiophen-3-yl)oxy)phenyl) acrylic acid, or pharmaceutically acceptable salt thereof, and (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide, or a pharmaceutically acceptable salt thereof, for the manufacture of a medicament for the treatment of ER+ breast cancer.

In another embodiment, is a method of treating a cancer, preferably breast cancer, comprising administrating to a patient in need thereof a pharmaceutical combination of (E)-3-(4-((2-(2-(1,1-difluoroethyl)-4-fluorophenyl)-6-hydroxybenzo[b]thiophen-3-yl)oxy)phenyl)acrylic acid, or pharmaceutically acceptable salt thereof, and (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide, or a pharmaceutically acceptable salt thereof, or a pharmaceutical composition comprising a pharmaceutical combination of (E)-3-(4-((2-(2-(1,1-difluoroethyl)-4-fluorophenyl)-6-hydroxybenzo[b]thiophen-3-yl)oxy)phenyl) acrylic acid, or pharmaceutically acceptable salt thereof, and (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide, or a pharmaceutically acceptable salt thereof and at least one pharmaceutically acceptable carrier.

In another embodiment, is a method of treating wild-type ER+ breast cancer comprising administrating to a patient in need thereof a pharmaceutical combination of (E)-3-(4-((2-(2-(1,1-difluoroethyl)-4-fluorophenyl)-6-hydroxybenzo[b]thiophen-3-yl)oxy)phenyl)acrylic acid, or pharmaceutically acceptable salt thereof, and (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide, or a pharmaceutically acceptable salt thereof, or a pharmaceutical composition comprising a pharmaceutical combination of (E)-3-(4-((2-(2-(1,1-difluoroethyl)-4-fluorophenyl)-6-hydroxybenzo[b]thiophen-3-yl)oxy)phenyl)acrylic acid, or pharmaceutically acceptable salt thereof, and (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide, or a pharmaceutically acceptable salt thereof and at least one pharmaceutically acceptable carrier.

In another embodiment, is a method of treating ER+ breast cancer, wherein said ER+ breast cancer contains ESR1 mutations, comprising administrating to a patient in need thereof a pharmaceutical combination of (E)-3-(4-((2-(2-(1,1-difluoroethyl)-4-fluorophenyl)-6-hydroxybenzo[b]thiophen-3-yl)oxy)phenyl)acrylic acid, or pharmaceutically acceptable salt thereof, and (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide, or a pharmaceutically acceptable salt thereof, or a pharmaceutical composition comprising a pharmaceutical combination of (E)-3-(4-((2-(2-(1,1-difluoroethyl)-4-fluorophenyl)-6-hydroxybenzo[b]thiophen-3-yl)oxy)phenyl)acrylic acid, or pharmaceutically acceptable salt thereof, and (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide, or a pharmaceutically acceptable salt thereof and at least one pharmaceutically acceptable carrier.

In a further embodiment, the mutations are selected from the group consisting of D538G, E380Q, Y537S, Y537N and Y537C.

In a further embodiment, the mutations are selected from D538G and Y537S.

In another embodiment, (E)-3-(4-((2-(2-(1,1-difluoroethyl)-4-fluorophenyl)-6-hydroxybenzo[b]thiophen-3-yl)oxy)phenyl)acrylic acid is administered orally at a dose of about 100 mg per day, or 200 mg per day, or 300 mg per day, or 400 mg per day, or 500 mg per day, or 600 mg per day.

In a further embodiment, (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide is administered orally at a dose of about 50 mg per day, or 100 mg per day, or 150 mg per day, or 200 mg per day, or 250 mg per day, or 300 mg per day, or 350 mg per day, or 400 mg per day, or 450 mg per day, in a single dose or in divided doses up to four times a day.

In a further embodiment, (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide is administered orally at a dose of about 50 mg per day, or 100 mg per day, or 150 mg per day, or 200 mg per day, or 250 mg per day, or 300 mg per day, or 350 mg per day, or 400 mg per day, or 450 mg per day, continuously.

In a further embodiment, (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide is administered orally at a dose of about 50 mg per day, or 100 mg per day, or 150 mg per day, or 200 mg per day, or 250 mg per day, or 300 mg per day, or 350 mg per day, or 400 mg per day, or 450 mg per day, with food.

In a further embodiment, (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide is administered orally at 200 mg per day. In a further embodiment, (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide is administered orally at a dose of about 300 mg per day. In a further embodiment, (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide is administered orally at a dose of about 400 mg per day.

Pharmacology and Utility

Breast cancer is a leading cause of cancer mortality among women. Though often generalized as a single disease, breast cancer is more commonly classified in a clinical setting by its molecular subtype, arising from the characterization of three key biomarkers. The presence or absence of the receptors estrogen and progesterone lead to a hormone receptor classification (HR+/HR−) while increased or decreased levels of the human epidermal growth factor receptor 2 (HER2) lead to a HER2 protein classification (HER2+/HER2−). Nearly 74% of breast cancers demonstrate high expression of the estrogen receptor-α (ERα), a nuclear hormone receptor directly implicated in the progression of HR+ cancers. This ligand-inducible transcription factor binds the hormone estrogen to activate and promote the expression of oncogenic genes.

In patients with ERα positive breast cancer, treatment has long relied on endocrine therapies such as tamoxifen (and its active metabolite, 4-hydroxytamoxifen) and anastrozole, both of which prevent ligand activation and ultimately gene expression. Tamoxifen, the primary standard of care for such patients, functions as an estrogen receptor modulator effectively blocking the binding of estrogen to the receptor and blocking its effects in breast tissue. Women treated with this first-line therapy often respond positively and show increased survival in clinical settings, but acquired resistance in these patients, ultimately leading to disease relapse, remains a significant medical challenge. Though the specific mechanism through which ERα positive tumors develop resistance to tamoxifen is not fully understood, aromatase inhibitors, such as letrazole have shown clinical efficacy in such refractory cancers. In contrast to tamoxifen, aromatase inhibitors owe their activity to the reduction in estrogen production, more specifically by inhibiting the enzyme responsible for the key biosynthetic step in the formation of estrogen. Unfortunately, as with tamoxifen, aromatase inhibitors can also lead to resistant cancer.

Fulvestrant is a selective estrogen receptor degrader (SERD) approved for treatment of endocrine resistant cancer. This steroid-based anti-estrogen both binds and accelerates the degradation of the estrogen receptor and is clinically effective in endocrine treated patients whose disease has progressed. Fulvestrant is limited, however, in its clinical utility owing in large part to its poor physicochemical properties. The drug cannot be administered orally but instead the approved clinical dosage of 500 mg administered into the gluteal area in two 5 mL injections once-monthly, does not appear sufficient to fully occupy the receptor. LSZ102 was developed as an oral medication, with improved bioavailability while retaining desirable estrogen receptor degradative properties.

Phosphatidylinositol 3-kinases (PI3Ks) comprise a family of lipid kinases that catalyze the transfer of phosphate to the D-3' position of inositol lipids to produce phosphoinositol-3-phosphate (PIP), phosphoinositol-3,4-diphosphate ($PIP_2$) and phosphoinositol-3,4,5-triphosphate ($PIP_3$) that, in turn, act as second messengers in signaling cascades by docking proteins containing pleckstrin-homology, FYVE, Phox and other phospholipid-binding domains into a variety of signaling complexes often at the plasma membrane. Of the two Class 1 PI3Ks, Class 1A PI3Ks are heterodimers composed of a catalytic p110 subunit (α, β, δ isoforms) constitutively associated with a regulatory subunit that can be p85α, p55α, p50α, p85β or p55γ. The Class 1B sub-class has one family member, a heterodimer composed of a catalytic p110γ subunit associated with one of two regulatory subunits, p101 or p84. The modular domains of the p85/55/50 subunits include Src Homology (SH2) domains that bind phosphotyrosine residues in a specific sequence context on activated receptor and cytoplasmic tyrosine kinases, resulting in activation and localization of Class 1A PI3Ks. Class 1B PI3K is activated directly by G protein-coupled receptors that bind a diverse repertoire of peptide and non-peptide ligands. Consequently, the resultant phospholipid products of class I PI3K link upstream receptors with downstream cellular activities including proliferation, survival, chemotaxis, cellular trafficking, motility, metabolism, inflammatory and allergic responses, transcription and translation.

In many cases, PIP2 and PIP3 recruit Akt, the product of the human homologue of the viral oncogene v-Akt, to the plasma membrane where it acts as a nodal point for many intracellular signaling pathways important for growth and survival. Aberrant regulation of PI3K, which often increases survival through Akt activation, is one of the most prevalent events in human cancer and has been shown to occur at multiple levels. The tumor suppressor gene PTEN, which dephosphorylates phosphoinositides at the 3' position of the inositol ring and in so doing antagonizes PI3K activity, is functionally deleted in a variety of tumors. In other tumors, the genes for the p110α isoform, PIK3CA, and for Akt are amplified and increased protein expression of their gene products has been demonstrated in several human cancers. Furthermore, mutations and translocation of p85α that serve to up-regulate the p85-p110 complex have been described in human cancers. Finally, somatic missense mutations in PIK3CA that activate downstream signaling pathways have been described at significant frequencies in a wide diversity of human cancers. These observations show that deregulation of phosphoinositol-3 kinase and the upstream and downstream components of this signaling pathway is one of the most common deregulations associated with human cancers and proliferative diseases.

Inhibitors of PI3K alpha would, therefore, be of particular value in the treatment of proliferative disease and other disorders. Mutations in the PIK3CA gene are present in 28-47% of HR+ breast cancer. Critically, ER signaling and PI3K activity coregulate one another. Inhibition of either results in upregulation of the other thus simultaneous inhibition of both to achieve maximal anti-tumor activity is a rational approach.

On the basis of the inhibitory studies described in the "Examples" section below, the combination of LSZ102 and alpelisib shows therapeutic efficacy. Example 8 details the efficacy of LSZ102 and alpelisib as a combination tested in the orthotopic MCF-7 breast cancer model in mice. Single agent treatments of LSZ102 at 10 mg/kg QD and alpelisib at 20 mg/kg QD resulted in tumor growth inhibition (% ΔT/ΔC of 13% and 38%, respectively, on day 62). Surprisingly, the combination of the two induced a 32% tumor regression (Table 7).

Pharmaceutical Compositions

In another aspect, the present invention provides pharmaceutically acceptable compositions which comprise a therapeutically-effective amount LSZ102 and alpelisib, formulated together with one or more pharmaceutically acceptable carriers (additives) and/or diluents. As described in detail below, the pharmaceutical compositions of the present invention may be specially formulated for administration in solid or liquid form, including those adapted for oral administration, for example, drenches (aqueous or non-aqueous solutions or suspensions), tablets, e.g., those targeted for buccal, sublingual, and systemic absorption, boluses, powders, granules, pastes for application to the tongue.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al. (1977) "Pharmaceutical Salts", *J Pharm. Sci.* 66:1-19).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution, suspension or solid dispersion in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, troches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of the combination of the invention will be that amount of each compound which is the lowest dose effective to produce a therapeutic effect. Such an effective dose will generally depend upon the factors described above.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents.

EXAMPLES

LSZ102 and Alpelisib (E)-3-(4-((2-(2-(1,1-difluoroethyl)-4-fluorophenyl)-6-hydroxybenzo[b]thiophen-3-yl)oxy)phenyl)acrylic acid (LSZ102) is synthesized according to example 139 of WO2014/130310. (S)-Pyrrolidine-1,2-dicarboxylic acid 2-amide 1-({4-methyl-5-[2-(2,2,2-trifluoro-1,1-dimethylethyl)-pyridin-4-yl]-thiazol-2-yl}-amide (alpelisib) is synthesized according to example 15 of WO2010/029082.

The utility of LSZ102 and alpelisib described herein can be evidenced by testing in the following examples.

Example 1

LSZ102 Promotes ER Degradation in MCF-7 Cells

Western blot. For the analysis of LSZ102, fulvestrant, and tamoxifen on ERα protein levels in MCF-7 tumors at the end of efficacy study, snap frozen tumors were pulverized into a powder and then transferred to Lysing Matrix Tubes (MP Biomedicals Cat. #6913-500) mixed with cold lysis buffer (1× cell lysis buffer; Cell Signaling, Cat. #9803S) containing Complete Mini (1 tablet to 10 mL), PhosStop (1 tablet to 10 mL and 1 M Urea) homogenized by a Fast Prep 24 Tissue Lyser (MP Biomedicals). Total protein concentrations of the lysate were tested by BCA assay (Pierce BCA Protein Assay Kit, Prod #23225, Thermo Scientific) according to the manufacturer's instructions. Lysates were separated by SDS-PAGE, transferred onto membranes, and then immunoblotted using an anti-ERα antibody (Santa Cruz Biotechnology, HC-20), as well as an anti-tubulin antibody as a loading control. Western blots were scanned for quantification of the immunoblotted bands. The percent of ERα remaining was determined by comparing tumors from the treated mice versus those from the vehicle control group. FIG. 1 demonstrates that LSZ102 promotes ER degradation in MCF-7 cells in comparison to fulvestrant and tamoxifen, ER degradation by LSZ102 is similar to fulvestrant at equivalent concentrations, and no effect on ER degradation was observed with tamoxifen in MCF-7 cells. These results suggest that LSZ102 can degrade ER levels similar to fulvestrant and will inhibit ER activity over a similar concentration range.

Example 2

LSZ102 Anti-Proliferation and ER Degradation Activity in MCF-7 Parental and Y537S Cells The effects of LSZ102, fulvestrant, and tamoxifen as single agents were studied in MCF-7 parental (ER wildtype, or WT) and ER Y537S mutant cells. MCF-7 WT cells and Y537S mutant cells were incubated in RPMI (without phenol red) plus 10% charcoal dextran-stripped serum and treated with escalated concentration of compounds in the presence of 0.1 nM (nanomolar) estradiol (WT) or no estradiol (Y537S). Cell viability was determined by CellTiter-Glo (CTG) assay after 7 days of compound treatment. For ERE-luciferase assay, cell luciferase signal was measured using Bright-Glo assay after 24 hours. The IC50 value is the compound concentration which inhibits 50% of the CTG signal by 50%. IC50 nM values were calculated using the XLfit software and are defined as the inflection point of the fitted inhibition curves. The results for anti-proliferation activity of LSZ102, fulvestrant, and tamoxifen in MCF-7 WT and Y537S mutant cells are presented in Table 1.

TABLE 1

| Compound | MCF-7 proliferation Ave IC50 (nM) | |
|---|---|---|
| | ESR1 WT | ESR1 Y537S |
| LSZ102 | 5.2 +/− 0.5 | 27.0 +/− 5.1 |
| Fulvestrant | 2.6 +/− 0.2 | 53.0 +/− 11.9 |
| Tamoxifen | 4.5 +/− 1.0 | 60.1 +/− 10.4 |

In MCF-7 WT cells, the inhibition of cell proliferation by LSZ102, fulvestrant, and tamoxifen was similar. LSZ102 was found to inhibit cell proliferation in MCF-7 WT cells at an IC50 of 5.2 nM while fulvestrant inhibited cell proliferation at 2.6 nM and tamoxifen at 4.5 nM. In MCF-7 Y537S mutant cells, the inhibition of cell proliferation with LSZ102 was the most potent of the three. LSZ102 was found to inhibit cell proliferation in MCF-7 ER Y537S mutant cells at an IC50 value of 27.0 nM while fulvestrant inhibited cell proliferation at 53.0 nM and tamoxifen at 60.1 nM. While all three compounds had a shift in IC50 efficacy from the MCF-7 WT to the Y537S mutant, LSZ102 was the least shifted and retained the most potent anti-proliferation activity of the three compounds tested. This data suggests that LSZ102 would have more suppressive activity of the ESR1 Y537S mutant in patients.

Figure 2A:
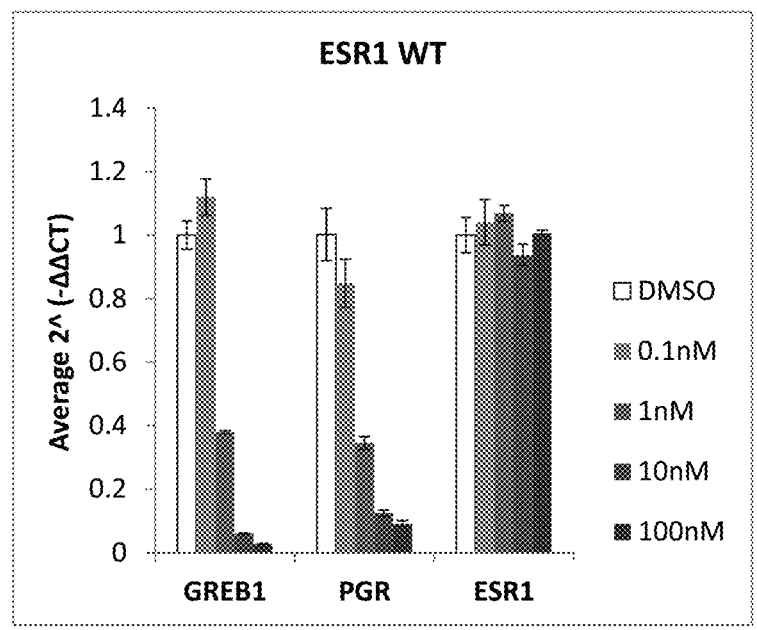
FIG. 2A: PCR analysis of mRNA in LSZ102-treated MCF-7 parental (WT) cells.
Figure 2B:
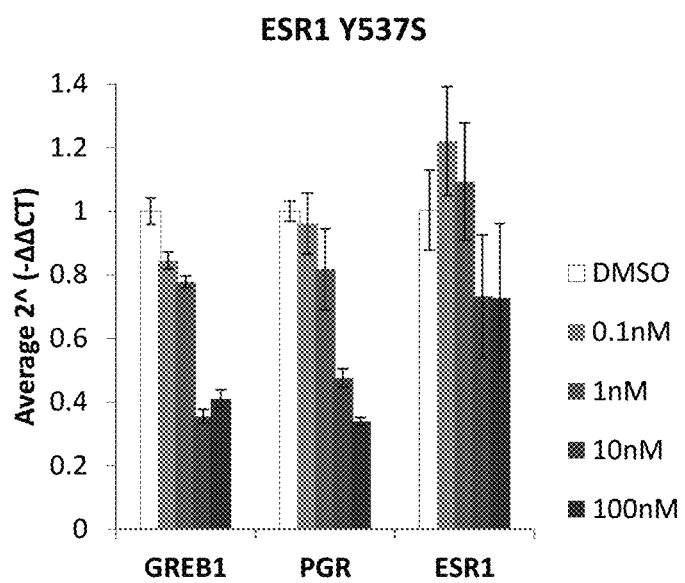
FIG. 2B: PCR analysis of mRNA in LSZ102-treated MCF-7 Y537S mutant cells.

PCR analysis. mRNA from LSZ102-treated MCF-7 WT and Y537S mutant cells were isolated and subjected to qRT-PCR analysis for ER target genes expression (FIGS. 2A and 2B). The mRNA levels of canonical ER target genes GREB1 and PGR were measured against mRNA expression of ER (ESR1), as a control for LSZ102's effect on ER itself, to ensure that the effects are not due to effects on ER mRNA levels but instead on ER protein levels. LSZ102 exhibited a dose response inhibition for the mRNA expression of both GREB1 and PGR in the MCF-7 WT and Y537S mutant cells. The effect was more pronounced in the WT cells, but at high concentrations, GREB1 and PGR expression were significantly reduced. In contrast, ESR1 mRNA levels were not significantly reduced in either cell line. This data demonstrates the anti-proliferation effect of LSZ102 in MCF-7 Y537S mutant cells is due to suppression of ER activity as measured by the ER target genes GREB1 and PGR. This points to the effect on LSZ102 being both on target and sufficient to block ER transcription.

Figure 3:
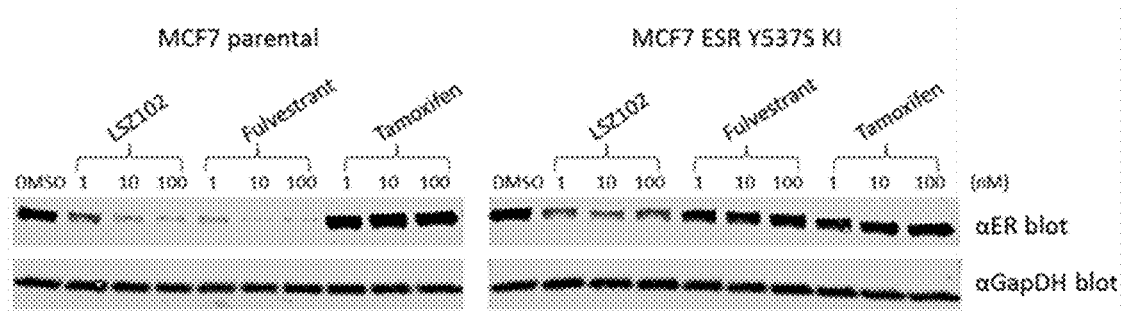
FIG. 3: Comparison of ERα degradation activity of LSZ102, fulvestrant and tamoxifen in MCF-7 parental (WT) and Y537S mutant cells.

Immunoblot analysis. MCF-7 parental and Y537S mutant cells were grown in phenol red free RPMI media with 10% charcoal dextran stripped serum continuously (Y537S mutant) or for 3 days (parental) followed with 24 hr treatment with LSZ102, fulvestrant, and tamoxifen as single agents. Extracted cell lysates were subjected to immunoblot analysis (FIG. 3) for ERα protein quantification. In the MCF-7 parental cells, both LSZ102 and fulvestrant significantly reduce ER protein levels over a dose response. In the MCF-7 Y537S mutant cells, LSZ102 dramatically reduced ER protein levels across doses but fulvestrant did not appear to have any effect. This data clearly demonstrates that LSZ102 can still bind and degrade mutant ESR1 Y537S in cells and that this degradation results in both an inhibition of ER transcription and ER driven proliferation induced by estrogen.

Example 3

MCF-7 Xenograft Model in NSG Mice

Figure 4:
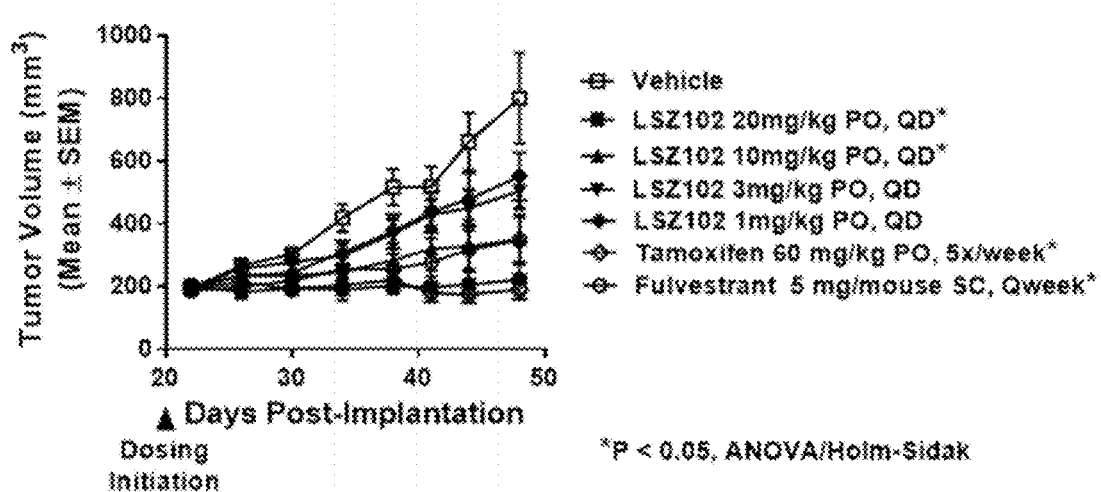
FIG. 4: Anti-tumor efficacy of LSZ102, fulvestrant and tamoxifen in the orthotopic human breast cancer MCF-7 xenograft model.

The estrogen response ER positive (ER+) MCF-7 cell line was shown to be sensitive to LSZ102 in vitro. To demonstrate targeted anti-tumor activity in the orthotopic MCF-7 xenograft model in NOD scid gamma (NSG) mice, 1, 3, 10 and 20 mg/kg of LSZ102 was administered orally (PO) once daily (QD) along with 5 mg of fulvestrant administered subcutaneously (SC) once weekly (Qweek) per mouse and 60 mg/kg of tamoxifen administered orally (PO) once daily for 5 days per week as positive controls (FIG. 4). Mice were supplemented with estradiol (0.72 mg estradiol/90-day release pellets) to further support MCF-7 tumor growth several days prior to cell implantation. MCF-7 tumors were established in female NSG mice by injection of $10 \times 10^6$ cells in 50% Matrigel® into the axillary mammary fat pad area of each mouse. When tumors reached an average of 200 mm$^3$, mice were randomized according to tumor volume into treatment groups (n=8). The effect of the treatments on tumor response in the MCF-7 breast cancer xenograft model on Day 48 are presented in Table 2.

TABLE 2

| Compound | Dose, Schedule | Tumor response ΔT/ΔC (%) | Regression (%) |
|---|---|---|---|
| Vehicle | None PO, QD | 100 | — |
| LSZ102 | 1 mg/kg, PO, QD | 56 | — |
| LSZ102 | 3 mg/kg, PO, QD | 51 | — |
| LSZ102 | 10 mg/kg, PO, QD | 25* | — |
| LSZ102 | 20 mg/kg, PO, QD | 2* | — |
| Tamoxifen | 60 mg/kg, PO, QD × 5 days × QWeek | −0.8* | 1* |
| Fulvestrant | 5 mg/mouse SC, QWeek | 24* | — |

*p < 0.05 versus vehicle (One-way ANOVA/Holm-Sidak post-hoc test)

LSZ102 treatment resulted in dose dependent anti-tumor efficacy with maximal activity observed in mice, treated with the dose of 20 mg/kg QD, corresponding to a percentage of mean change in tumor volume vs control (ΔT/ΔC) of 2.4% (Day 48, p<0.05). At the dose of 20 mg/kg QD, tumor stasis was achieved and maintained for 48 days. The 10 mg/kg QD dose was also significantly efficacious (ΔT/ΔC=25%, p<0.05), while the 1 and 3 mg/kg QD doses were not significantly effective (% ΔT/ΔC of 51% and 56%, respectively). Tamoxifen and fulvestrant, used as controls, induced tumor stasis and a suppression of growth, respectively.

Example 4

ER+ Primary Breast Cancer Model HBRX1298 in NSG Mice

Figure 5:
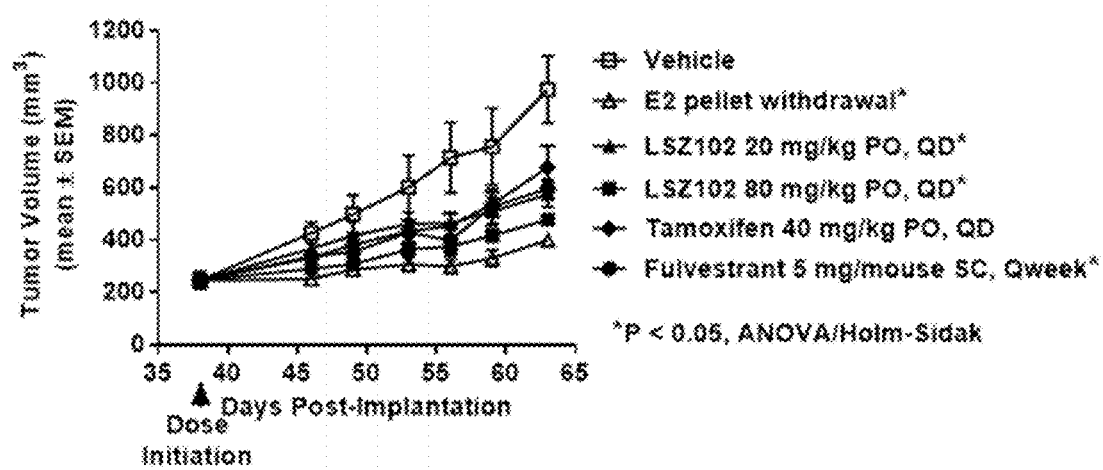
FIG. 5: Anti-tumor efficacy of LSZ102, fulvestrant and tamoxifen in the primary human breast cancer HBRX1298 xenograft model.

The ER+ primary breast cancer model HBRX1298, which is sensitive to estrogen, was tested in NSG mice under the following conditions: LSZ102 20 mg/kg PO QD, LSZ102 80 mg/kg PO QD, tamoxifen 40 mg/kg PO QD, fulvestrant 5 mg/mouse SC, weekly, vehicle control and control with estradiol timed-release pellet removal (FIG. 5). The effect of the treatments on tumor response in the HBRX1298 breast cancer xenograph model on Day 63 are presented in Table 3.

TABLE 3

| Test agent | Dose, Schedule | Tumor response ΔT/ΔC (%) |
|---|---|---|
| Vehicle | None PO, QD | 100 |
| Vehicle, but with Estradiol pellet removal | None PO, QD | 21* |
| LSZ102 | 20 mg/kg PO, QD | 45* |
| LSZ102 | 80 mg/kg PO, QD | 32* |
| Tamoxifen | 40 mg/kg PO, QD | 59 |
| Fulvestrant | 5 mg/mouse SC, QWeek | 48* |

*p < 0.05 versus vehicle (One-way ANOVA/Holm-Sidak post-hoc test).

HBRX1298 tumors were established in NSG female mice by injection of a tumor brei into the inguinal mammary fat pad area. Mice were implanted with 0.72 mg estradiol/90-day release pellets several days prior to cell implantation. When tumors reached approximately 250 mm3, mice were randomized according to tumor volume into treatment groups (n=6 for all, except n=4 for estradiol withdrawal) on Day 38. There was an efficacy benefit at doses of 20 and 80 mg/kg QD of LSZ102. The 80 mg/kg QD dose of LSZ102 showed statistically significant efficacy over vehicle treated controls and comparable efficacy to that seen in mice with estradiol pellet removal. The 80 mg/kg QD dose inhibited tumor volumes close to the extent observed in mice with estradiol pellet removal (% ΔT/ΔC=32% and 21%, respectively; p<0.05).

Example 5

Y537S ER Mutant MCF-7 Breast Cancer Model in NSG Mice

Figure 6:
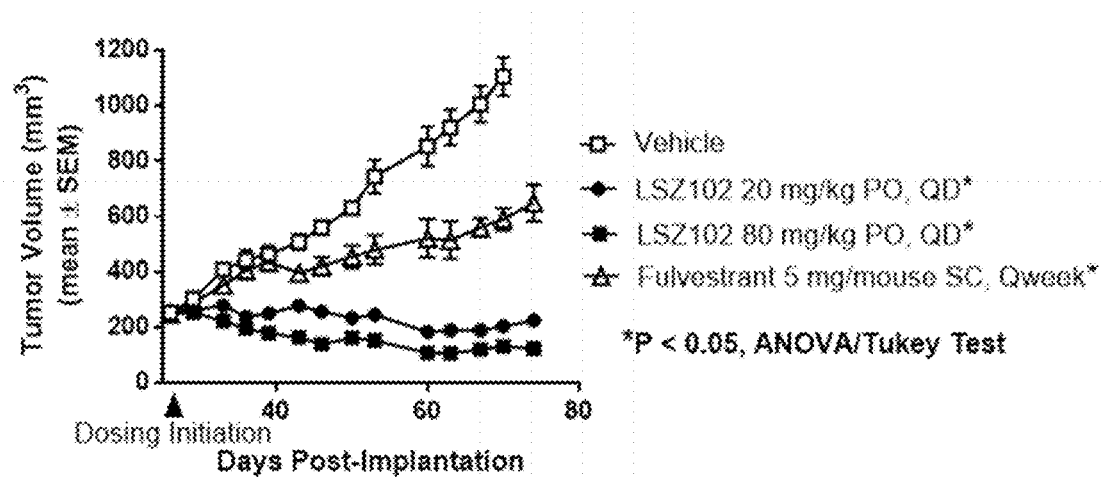
FIG. 6: Efficacy of LSZ102 and fulvestrant in the Y537S ER mutant MCF-7 breast cancer xenograft model.

The Y537S ER mutant MCF-7 breast cancer model was tested in NSG mice under the following conditions: LSZ102 20 mg/kg PO QD, LSZ102 80 mg/kg PO QD, fulvestrant 5 mg/mouse SC weekly, and vehicle control (FIG. 6). The effect of the treatments on tumor response in the Y537S ER mutant MCF-7 breast cancer model on Day 70 are presented in Table 4.

TABLE 4

| Test agent | Dose, Schedule | Tumor response | |
|---|---|---|---|
| | | ΔT/ΔC (%) | Regression (%) |
| Vehicle | None PO, QD | — | — |
| LSZ102 | 20 mg/kg, QD, PO | −5.5 | 17.7 |
| LSZ102 | 80 mg/kg, QD, PO | −13.9 | 46.9 |
| Fulvestrant | 5 mg/mouse SC, QWeek | 39.4 | none |

*$p < 0.05$ versus vehicle (One-way ANOVA/Tukey post-hoc test).

The MCF-7 cell line was engineered using CRISPR technology to knock out the innate wild type functional ER and knock-in mutant Y537S ER. Ovariectomized female NSG mice were implanted with 10×10$^6$ cells in 50% Matrigel® into the axillary mammary fat pad area of each mouse. When tumors reached an average of 250 mm$^3$, mice were randomized according to tumor volume into treatment groups.

Daily LSZ102 treatment at 20 and 80 mg/kg regressed the Y537S ER expressing MCF-7 xenografts demonstrating activity in breast cancers expressing this mutant form of ER, while fulvestrant did not reach statistically significant efficacy.

Example 6

D538G ER Mutant MCF-7 Breast Cancer Model in NSG Mice

Figure 7A:
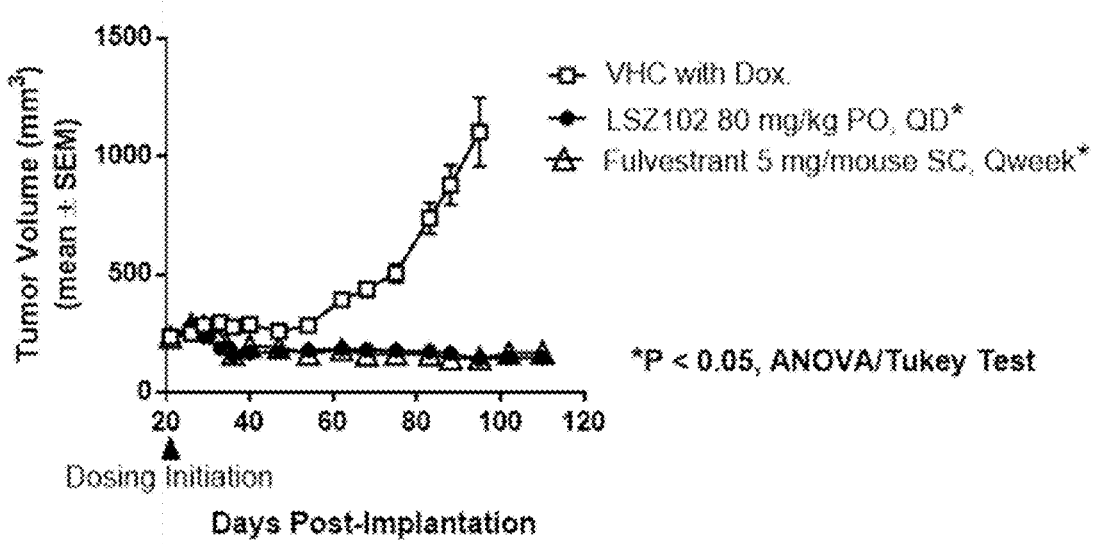
FIG. 7A: Efficacy of LSZ102 and fulvestrant in the D538G ER mutant MCF-7 breast cancer xenograft model.

The D538G doxycycline-inducible ER mutant MCF-7 breast cancer model was tested in NSG mice under the following conditions: LSZ102 80 mg/kg PO QD, fulvestrant 5 mg/mouse SC weekly, and vehicle control (FIG. 7A). The effect of the treatments on tumor response in the D538G ER mutant MCF-7 breast cancer model on Day 74 are presented in Table 5.

TABLE 5

| Test agent | Dose, Schedule | Tumor response | |
|---|---|---|---|
| | | ΔT/ΔC (%) | Regression (%) |
| Vehicle | None PO, QD | — | — |
| LSZ102 | 80 mg/kg, QD, PO | −89.3 | 37.7 |
| Fulvestrant | 5 mg/mouse SC, QWeek | −66.5 | 28.1 |

*$p < 0.05$ versus vehicle (One-way ANOVA/Tukey post-hoc test).

The MCF-7 cell line was engineered with a doxycycline-induced promoter to express the D538G mutant ER. Ovariectomized female NSG mice were implanted with 10×10$^6$ cells in 50% Matrigel® into the axillary mammary fat pad area of each mouse. Eight days after cell implantation, mice received doxycycline via the mouse chow. When tumors reached an average of 250 mm$^3$, mice were randomized according to tumor volume into treatment groups.

Daily 80 mg/kg of LSZ102 regressed the D538G ER expressing MCF-7 xenografts demonstrating activity in breast cancers expressing this mutant form of ER, while fulvestrant was also active.

Figure 7B:
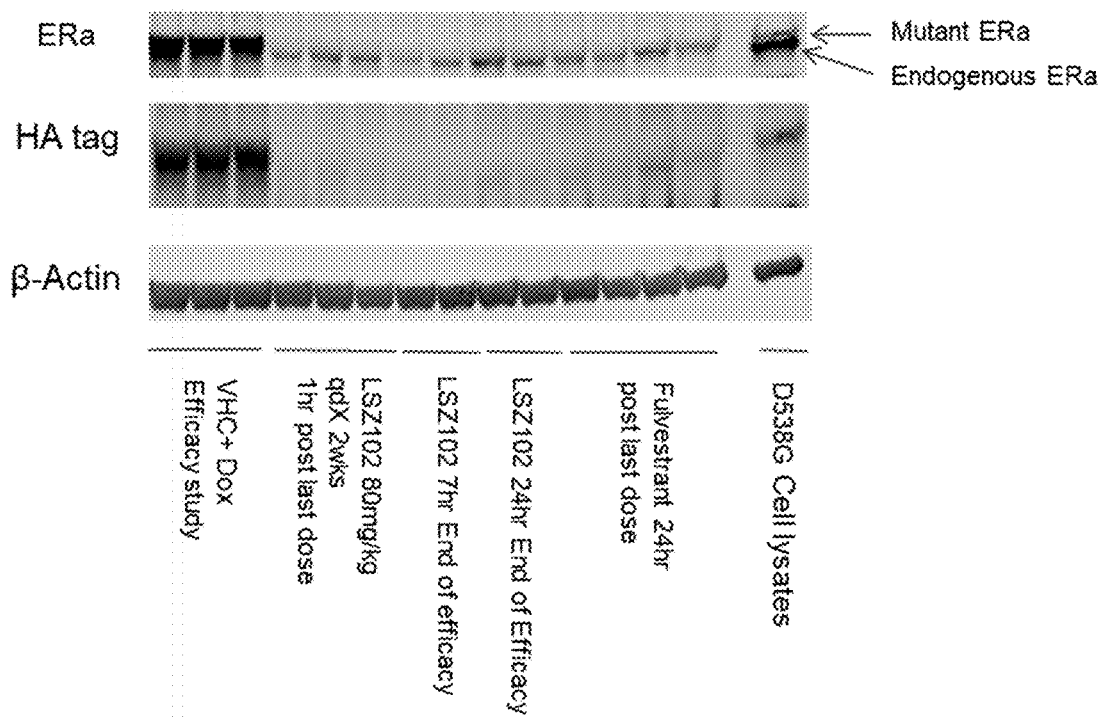
FIG. 7B: ERα degradation activity of LSZ102 and fulvestrant in D538G ER mutant MCF-7 cells.

Protein was isolated from tumors at the end of the efficacy for use in a western blot analysis (FIG. 7B). The membrane was immunostained with an anti-ER or anti-hemagglutinin (HA) antibody since the mutant ER protein was HA tagged. The membrane was also stained for β-actin to serve as a loading control. A set of protein samples from tumors collected after two weeks of dosing with LSZ102 was also included. The samples show degradation of this D538G mutant ER protein.

Example 7

Dose Fractionation Study of LSZ102 in Mice with MCF-7 Xenografts

Figure 8A:
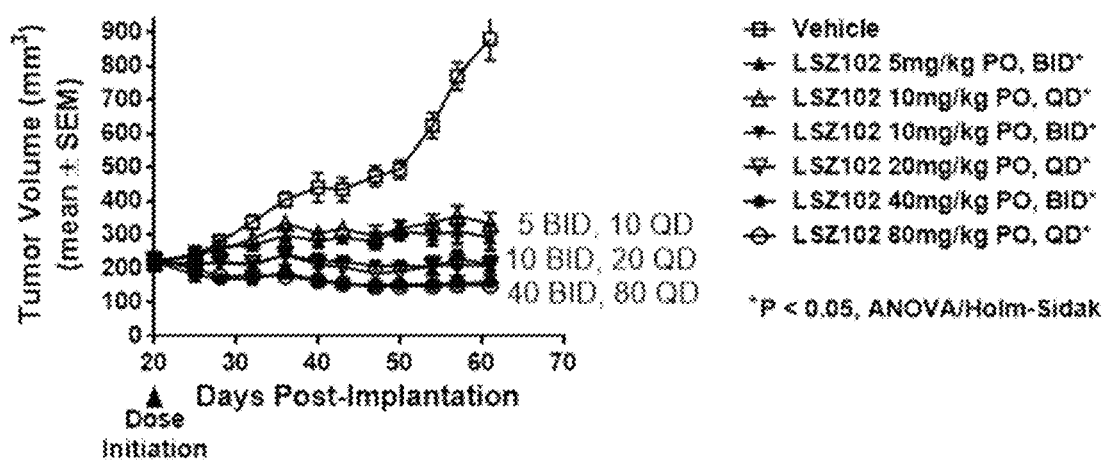
FIG. 8A: Impact of the LSZ102 dose fractionation on efficacy in the MCF-7 xenograft model.

A dose fractionation study of LSZ102 in mice with MCF-7 xenografts to assess the effect of QD dosing versus split-dose twice daily (BID) dosing showed equivalent efficacy suggesting that LSZ102 is driven by total exposure (FIG. 8A). The single agent LSZ102 dose response induced a concentration dependent tumor regression in the MCF-7 breast cancer xenograft model on Day 61. The effect of the treatments on tumor response in the MCF-7 breast cancer xenograft model on Day 61 is presented in Table 6.

TABLE 6

| Test agent | Dose, Schedule | Tumor response | |
|---|---|---|---|
| | | ΔT/ΔC (%) | Regression (%) |
| Vehicle | None PO, QD | 100* | — |
| LSZ102 | 5 mg/kg, PO, BID | 11* | — |
| LSZ102 | 10 mg/kg, PO, QD | 16* | — |
| LSZ102 | 10 mg/kg, PO, BID | −1* | — |
| LSZ102 | 20 mg/kg, PO, QD | −2* | 5* |
| LSZ102 | 40 mg/kg, PO, BID | −8* | 21* |
| LSZ102 | 80 mg/kg PO, QD | −11* | 31* |
| Tamoxifen | 60 mg/kg, PO, 5QW | −4* | 11* |
| Fulvestrant | 5 mg/mouse SC, QWeek | 18* | — |

*$p < 0.05$ versus vehicle (One-way ANOVA/Holm-Sidak post-hoc test).

Figure 8B:
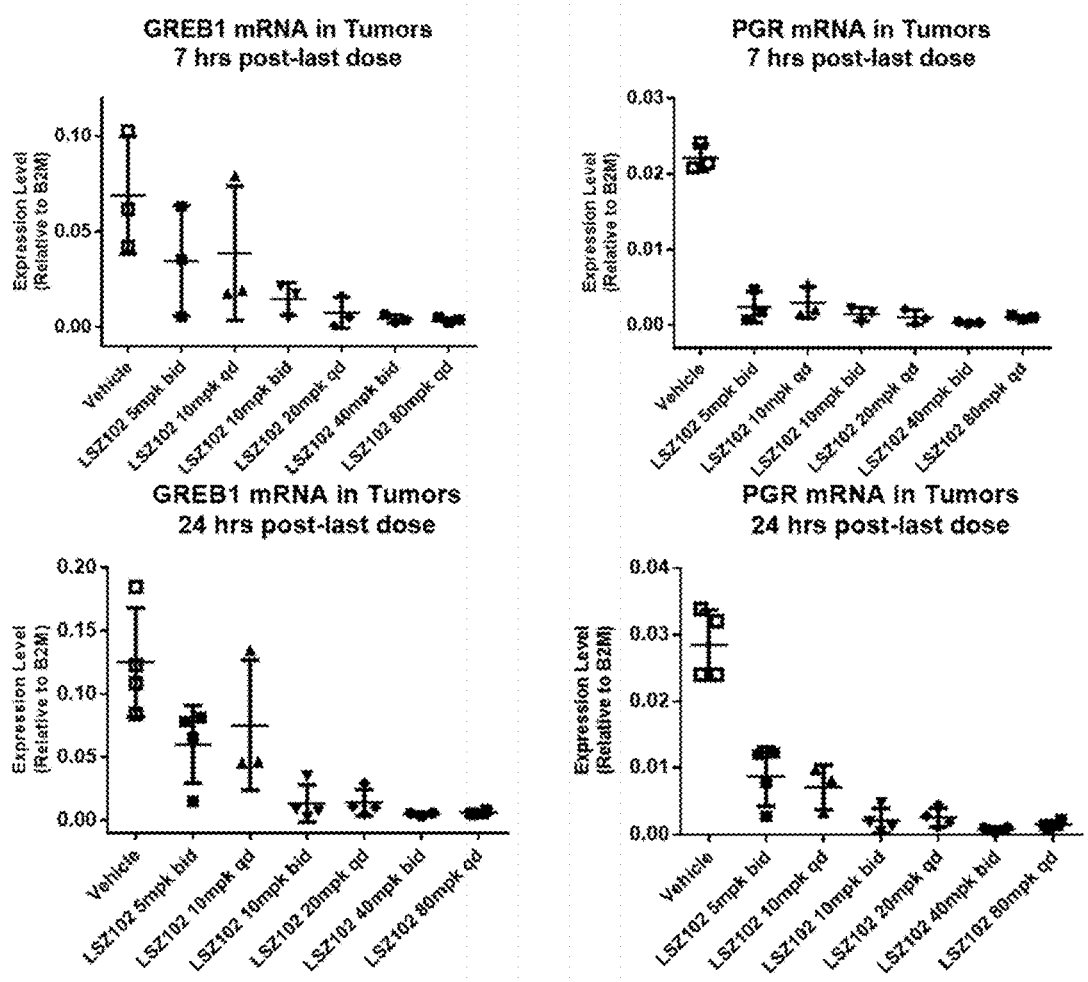
FIG. 8B: Impact of LSZ102 dose fractionation on ER regulated transcripts GREB1 and PGR mRNA levels.

Following a final treatment on day 61, tumors collected after 24 hours showed that the higher dose levels provided stronger inhibition of ER regulated transcripts GREB1 and PGR mRNA levels during the 24 hours dose intervals, but the PD between QD dosing and the BID split dose were the same (FIG. 8B). Data is plotted for individual animals and is normalized to expression of beta-2 microglobulin (B2M).

Example 8

Figure 9:
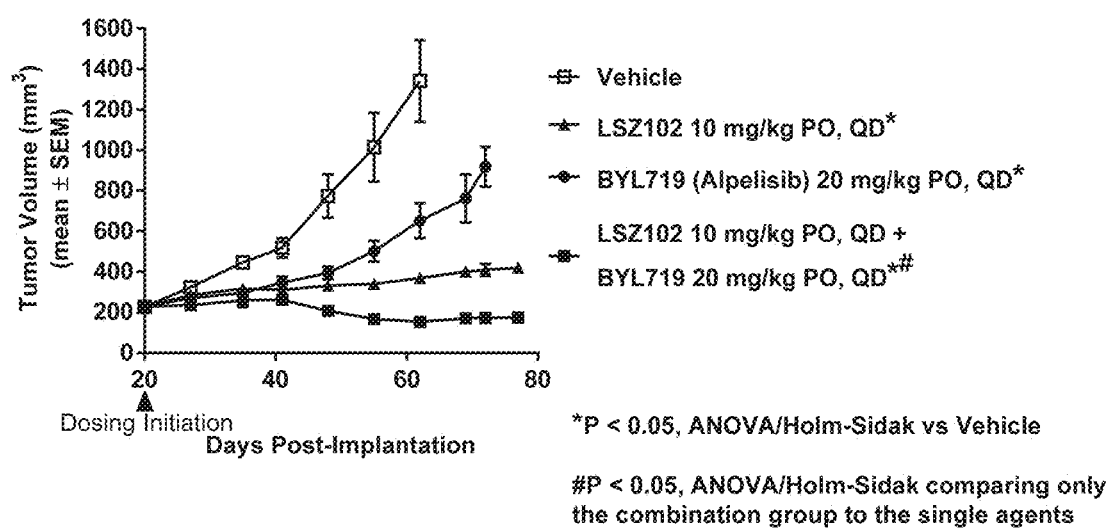
FIG. 9: Anti-tumor efficacy of LSZ102 in combination with alpelisib (BYL719) in the orthotopic human breast cancer MCF-7 xenograft model.

LSZ102 in Combination with Alpelisib in the ER+MCF-7 Breast Cancer Model in Mice The efficacy of LSZ102 and alpelisib as a combination was tested in the orthotopic MCF-7 breast cancer model in mice (FIG. 9). Tumor growth inhibition (% ΔT/ΔC of 13% and 38%) on day 62 was observed with single agent treatments of LSZ102 at 10 mg/kg QD and alpelisib at 20 mg/kg QD, respectively. Surprisingly, the combination of the two compounds induced a 32% tumor regression. Tumor regression was only observed in the combination treatment and not in the single agent LSZ102 or BYL719 treated MCF-7 breast cancer xenografts. The effect of the treatments on tumor response in the MCF-7 breast cancer model on Day 62 is presented in Table 7.

TABLE 7

| Test agent | Dose, Schedule | Tumor response ΔT/ΔC (%) | Regression (%) |
|---|---|---|---|
| Vehicle | None PO, QD | 100 | — |
| LSZ102 | 10 mg/kg, QD, PO | 13* | — |
| BYL719 | 20 mg/kg, QD, PO | 38 | — |
| LSZ102 + BYL719 | 10 mg/kg + 20 mg/kg QD, PO | −7*,# | 32*,# |

*p < 0.05 One Way ANOVA/Tukey post-hoc test, versus vehicle control..
p < 0.05 One Way ANOVA/Tukey post-hoc test or Holm-Sidak post-hoc test), comparing the combination group to the single agents LSZ102 or BYL719.

Example 9

Combination of LSZ102 with Alpelisib in MCF-7 Cells

Figure 10:
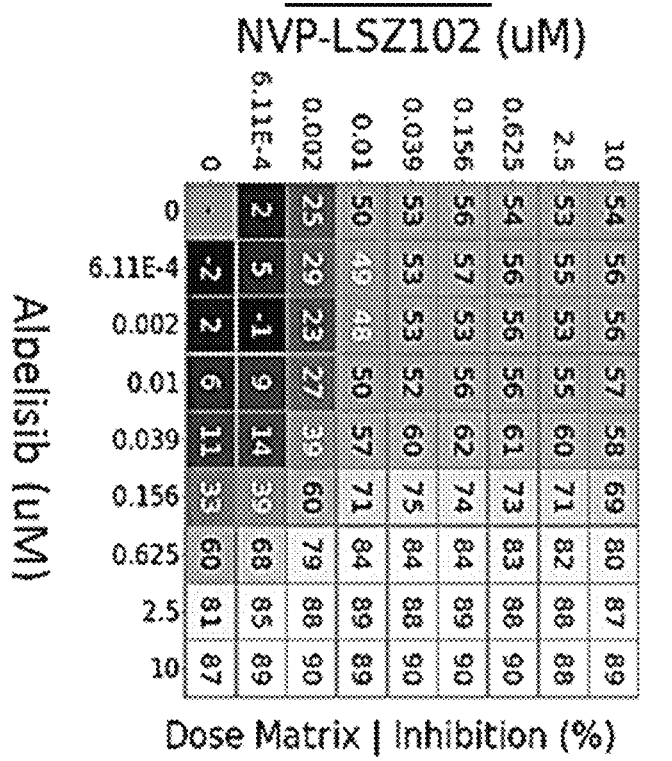
FIG. 10: Dose matrix and isobologram demonstrating the effects of combining LSZ102 with alpelisib (BYL719) on proliferation in the MCF-7 cell line in RPMI plus 10% full serum media.
Figure 10:
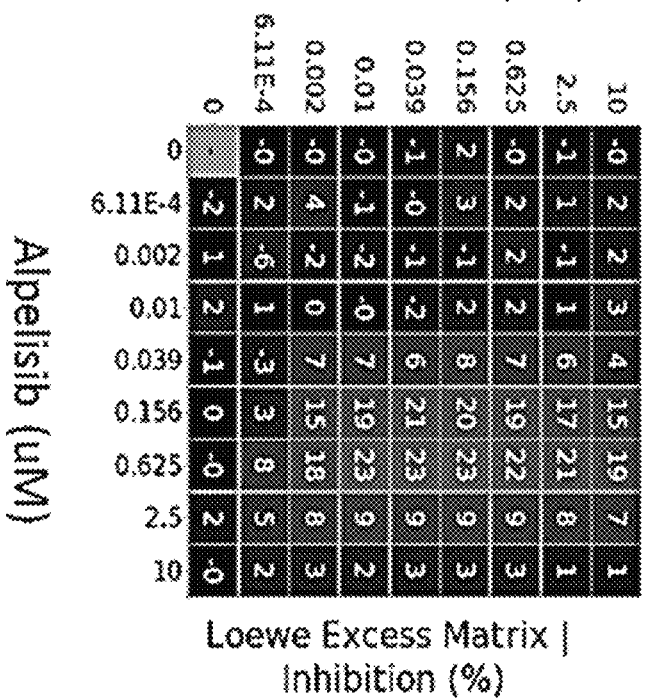

Proliferation assay. MCF-7 cells were cultured in RPMI medium plus 10% full serum media and treated with escalated concentrations of the combined compounds in checkerboard design. Cell viability was determined by CellTiter-Glo assay and normalized to Dimethyl sulfoxide (DMSO) control after 7 days of compound treatment. The percent growth inhibition and excess inhibition were analyzed using the Chalice software (CombinatoRx, Cambridge Mass.). Data was obtained with the Loewe algorithm, which calculates a weighted "Synergy Score" across the dose matrix that adjusts for dose sampling and coverage and weights to favor combination effects at high inhibition levels (Lehar et al. 2009). Synergy score and isobolograms were generated to quantify the combination strength. A synergy score higher than 2 was considered as significant when compared to the variation of synergy scores seen within self-crosses (drug-with-self; theoretical synergy score of 0) (Lehar et al. 2009). Excess inhibition was calculated using the Loewe synergy model which measures the effect on growth relative to what would be expected if two drugs behave in a dose additive manner. Positive numbers represent areas of increasing synergy. Synergistic anti-proliferative effects was observed with the combination of LSZ102 and alpelisib (synergy score=6.3) in MCF-7 cells in vitro in RPMI plus 10% full serum media (FIG. 10).

Figure 11:
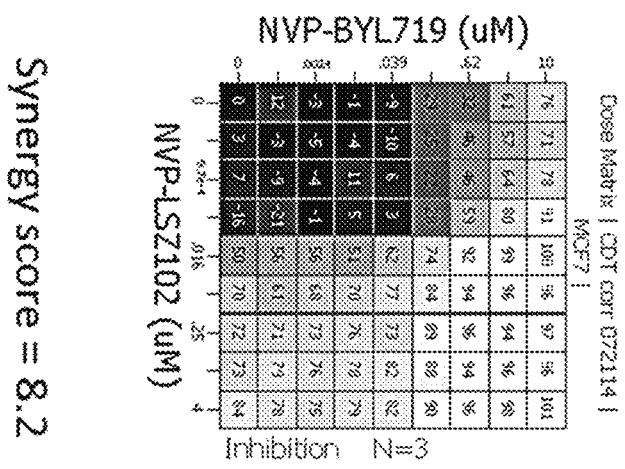
FIG. 11: Dose matrix and isobologram demonstrating the effects of combining LSZ102 with alpelisib (BYL719) in the MCF-7 cell lines in charcoal stripped serum with 0.1 nM E2 added.
Figure 11:
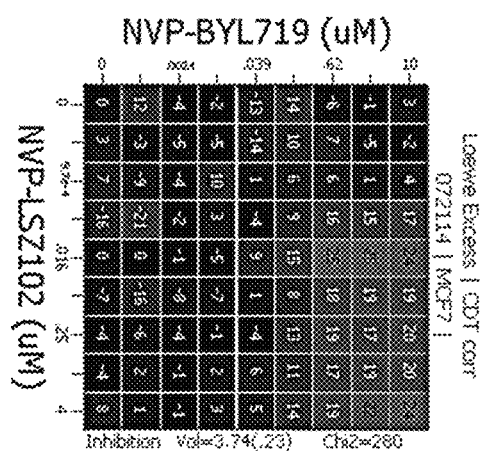
Figure 11:
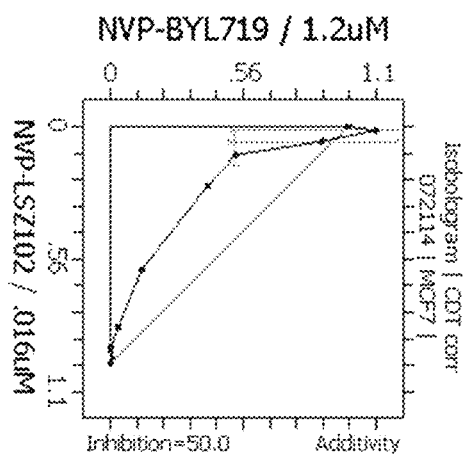
Figure 12:
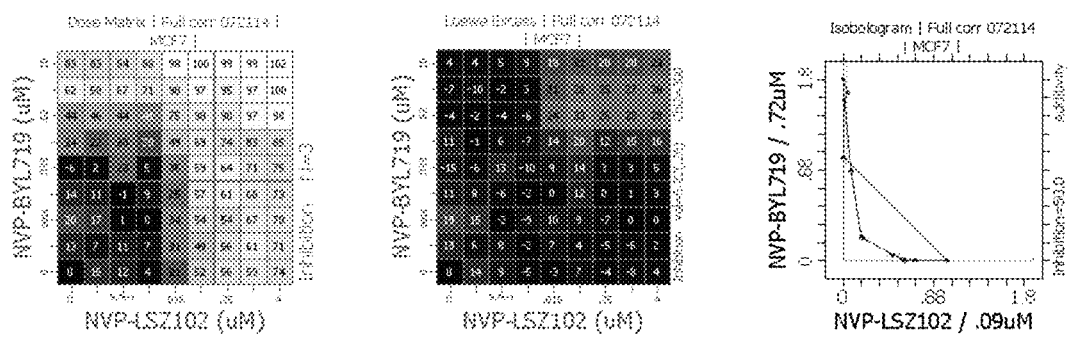
FIG. 12: Dose matrix and isobologram demonstrating the effects of combining LSZ102 with alpelisib (BYL719) in the MCF-7 cell line in full serum media.
Figure 13:
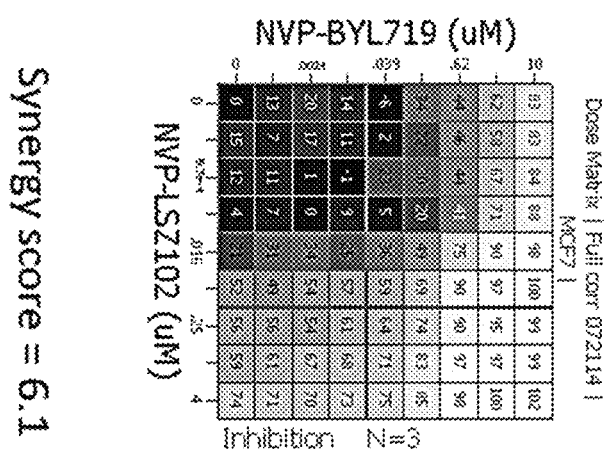

Combination cell growth and viability assays. Single-agent activity of alpelisib (BYL719) and LSZ102 was determined in MCF-7 cells BrDU assay (Thermo B23151). Briefly, cells were seeded in 96-well plates at roughly 8,000 to 10,000 cells per well depending on growth kinetics and were dosed in triplicate 24 hours later with a four-log dose range (0-10,000 nmol/L) of alpelisib (BYL719) and LSZ102. IC50 values were calculated using AUC at time points when cell indexes plateaued indicating confluency (roughly 96 hours posttreatment). To assess the combination efficacy of alpelisib (BYL719) and LSZ102, MCF-7 cells were seeded in 96-well plates and treated with the combination of alpelisib (BYL719) and LSZ102. Doses used in combination assays were based upon single-agent IC50 values determined by BrDU assay (Thermo B23151): cells were plated at 1,000 to 4,000 cells per well of a 96-well plate and dosed in triplicate 24 hours later with the same dose range of either compound. Viability was measured after 6 days with BrDU assay (Thermo B23151), and IC50 values were calculated. For combination studies, the dose selection included a range from ¼× to 4× (with × indicating single-agent IC50) and cells were plated in duplicate wells in a matrix format for treatment with both compounds. After 6 days of treatment, cell viability was measured using BrDU assay (Thermo B23151). Drug synergy was analyzed by isobologram and combination index methods, and synergy scores were determined by Chalice (FIGS. 11 and 12). These results clearly support the potential role for the combination of LSZ102 and alpelisib in the treatment of ER positive breast cancer.

Example 10

A Phase I/Ib Study of LSZ102±Alpelisib in Patients with Advanced or Metastatic ER+ Breast Cancer The primary objective is to: characterize the safety and tolerability with primary endpoints that include dose limiting toxicities (DLTs) and adverse events (AE); and identify a recommended dose and regimen of LSZ102 alone and/or in combination with alpelisib. Secondary objectives are to evaluate preliminary anti-tumor activity and looking at overall response rate (ORR), duration of response (DOR), progression-free survival (PFS), disease control rate (DCR), pharmacokinetics (PK) and pharmacodynamics (PD).

Eligible patients, ≥18 years old, have histologically confirmed ER+ breast cancer that has progressed after endocrine therapy for metastatic or locally advanced disease or recurrence while on, or within 12 months of the end of adjuvant treatment with an aromatase inhibitor.

All patients treated in the study received at least one dose of LSZ102. In the single agent dose escalation part of the study, LSZ102 was administered orally once-daily with a 200 mg starting dose, followed by QD doses of 400 mg, 450 mg, 600 mg, and 900 or BID doses of 225 mg and 300 mg. As of Jul. 23, 2018, 74 patients had been treated in the following dose groups: LSZ102 200 mg fasted QD (n=4), 400 mg QD fasted (n=6), 450 mg QD fasted (n=15), 450 mg QD with food (n=6), single 450 mg dose with a high fat meal (n=1), 600 mg QD fasted (n=20), 600 mg QD with food (n=4), 900 mg QD (n=6), 225 mg BID with food (n=6), and 300 mg BID with food (n=6). Median age was 59.5 years, 67.6% had ECOG performance status of zero, 58.9% had received prior fulvestrant therapy in metastatic setting and 57.5% had received prior CDK4/6 inhibitor therapy in metastatic setting, and 66/74 patients (89.2%) had discontinued treatment, mainly (59/74 patients (79.7%)) due to progressive disease. The baseline characteristics of these patients and disposition are summarized in tables 8 and 9, respectively, below.

TABLE 8

| Demographic Variable | LSZ102 Single agent arm (n = 74) |
|---|---|
| Age (years) Median (range) | 59.5 (30, 77) |
| ECOG PS, n (%) | |
| 0 | 50 (67.6) |
| 1 | 24 (32.4) |
| Prior lines of antineoplastic therapies in metastatic setting, n Median (min, max) | 4 (0, 10) |
| Prior lines of endocrine therapies in the metastatic setting, median (min, max) | 3 (0, 7) |
| Prior therapy in the metastatic setting | |

TABLE 8-continued

| Demographic Variable | LSZ102 Single agent arm (n = 74) |
|---|---|
| Fulvestrant, n (%) | 43 (58.9) |
| CDK4/6 inhibitor, n (%) | 42 (57.5) |

TABLE 9

| Demographic Variable | LSZ102 Single agent arm (n = 74) |
|---|---|
| Patients treated, n (%) | |
| Ongoing | 8 (10.8) |
| Discontinued | 66 (89.2) |
| Reason for discontinuation, n (%) | |
| Adverse event | 2 (2.7) |
| Progressive disease | 59 (79.7) |
| Subject/guardian decision | 4 (5.4) |
| Physician decision | 1 (1.4) |

Dose limiting toxicities (DLTs) occurred in four patients (5.9%): diarrhea in two patients of the LSZ102 900 mg QD fasted group, vomiting in one patient of the 600 mg QD fasted group, alanine aminotransferase increase in one patient of the LSZ102 450 mg QD with food group, and aspartate aminotransferase increase in one patient of the LSZ102 450 mg QD with food group.

Adverse events (AEs) of any grade ≥10% suspected to be related to single agent LSZ102 Arm A treatment period are summarized in Table 10. The most common (≥20%) drug-related adverse events were nausea (60.2%), diarrhea (53.4%), and vomiting (26.1%). Drug-related Grade 3 (G3) AEs were rarely reported: diarrhea (3 patients [4.1%]), nausea (2 patients [2.7%]), and vomiting (1 patient [1.4%]). A total of seven patients required dose reduction due to AEs, all of whom had gastrointestinal toxicities.

TABLE 10

| Preferred Term, n (%) | All Arm A Treatment Period patients (N = 73) | | |
|---|---|---|---|
| | G1 | G2 | G3 |
| Total | 38 (52.1) | 20 (27.4) | 7 (9.6) |
| Nausea | 32 (43.8) | 10 (13.7) | 2 (2.7) |
| Diarrhea | 25 (34.2) | 11 (15.1) | 3 (4.1) |
| Vomiting | 14 (19.2) | 4 (5.5) | 1 (1.4) |
| Decrease appetite | 11 (15.1) | 2 (2.7) | 0 |
| Constipation | 7 (9.6) | 1 (1.4) | 0 |
| Fatigue | 5 (6.8) | 3 (4.1) | 0 |

Preliminary evidence of anti-tumor activity was observed with single-agent LSZ102, with a disease control rate of 37.5%, as summarized in Table 11.

TABLE 11

| Parameter, n (%) | All LSZ102 single agent arm patients Evaluable, n = 72 |
|---|---|
| Complete response (CR) | 0 |
| Partial response (PR) | 1 (1.4) |
| Stable disease (SD) | 19 (26.4) |
| Non-CR/Non-PD | 7 (9.7) |
| Progressive disease (PD) | 40 (55.6) |
| Unknown | 6 (8.3) |
| Overall response rate (ORR) | 1 (1.4) |
| Disease control rate (DCR) | 27 (37.5%) |

Preliminary PK parameters demonstrate that LSZ102 has a short half-life (geometric mean across dose ranges: 3.1-5.6 hours), was rapidly absorbed (median $T_{max}$ 2-3 h) and showed dose-proportional increases in LSZ102 exposure; trough concentrations were above the predicted tumorostatic concentrations at doses ≥400 mg$^3$. Based on single dose PK, a high fat, high calorie meal resulted in an approximate 2-fold increase in LSZ102 exposure (AUC), compared to fasted conditions. Based on the 450 mg fasted and fed cohorts, LSZ102 exposure was not affected by dosing with a regular meal.

Oral single-agent LSZ102 appears well tolerated at doses up to 600 mg QD and at doses up to 300 mg BID, demonstrating antitumor activity, and achieving effective exposure levels based on PK and pharmacodynamics.

The dose escalation trial of LSZ102 in combination with alpelisib is ongoing wherein LSZ102 and alpelisib are administered orally at QD doses as follows: LSZ102 300 mg and alpelisib 200 mg (n=6), LSZ102 450 mg and alpelisib 200 mg (n=4), and LSZ102 300 mg and alpelisib 300 mg (n=6). As of Jul. 23, 2018, 13 patients continued ongoing treatment and 3 patients discontinued due to progressive disease. Based on clinical data, the combination is well tolerated and active.

It is understood that the Examples and embodiments described herein are for illustrative purposes only and that various modifications or changes in light thereof will be suggested to persons skilled in the art and are to be included within the spirit and purview of this application and scope of the appended claims.

What is claimed is:

1. A pharmaceutical combination comprising (E)-3-(4-((2-(2-(1,1-difluoroethyl)-4-fluorophenyl)-6-hydroxybenzo[b]thiophen-3-yl)oxy)phenyl)acrylic acid, or pharmaceutically acceptable salt thereof, and (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide, or a pharmaceutically acceptable salt thereof.

2. A pharmaceutical composition comprising the pharmaceutical combination according to claim 1 and at least one pharmaceutically acceptable carrier.

3. The pharmaceutical combination of claim 1 wherein (E)-3-(4-((2-(2-(1,1-difluoroethyl)-4-fluorophenyl)-6-hydrobenzo[b]thiophen-3-yl)oxy)phenyl)acrylic acid, or a pharmaceutically acceptable salt thereof, and (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide, or a pharmaceutically acceptable salt thereof, are in the same formulation.

4. The pharmaceutical combination of claim 1 wherein (E)-3-(4-((2-(2-(1,1-difluoroethyl)-4-fluorophenyl)-6-hydroxybenzo[b]thiophen-3-yl)oxy)phenyl)acrylic acid, or a pharmaceutically acceptable salt thereof, and (S)-Pyrrolidine-1,2-dicarboxylic acid 2-amide 1-({4-methyl-5-[2-(2,2, 2-trifluoro-1,1-dimethyl-ethyl)-pyridin-4-yl]-thiazol-2-yl}-amide, or a pharmaceutically acceptable salt thereof, are in separate formulations.

* * * * *